United States Patent [19]

Risch

[11] 4,056,360

[45] Nov. 1, 1977

[54] APPARATUS FOR DILUTION OF LIQUID SPECIMENS

[76] Inventor: Gerhard M. Risch, Schaan, Liechtenstein

[21] Appl. No.: 658,748

[22] Filed: Feb. 17, 1976

[30] Foreign Application Priority Data

Feb. 18, 1975  Germany .............................. 2506844

[51] Int. Cl.² ......................... B01L 3/02; G01N 1/14; G01N 1/18
[52] U.S. Cl. ..................................... 23/259; 73/425.6
[58] Field of Search .................... 23/259; 73/425.4 P, 73/425.6; 222/335

[56] References Cited

U.S. PATENT DOCUMENTS

| | | | |
|---|---|---|---|
| 1,098,514 | 6/1914 | Maddox | 23/259 X |
| 3,421,858 | 1/1969 | Quinn | 23/259 X |
| 3,646,817 | 3/1972 | Hinchman et al. | 73/425.6 |
| 3,660,037 | 5/1972 | Sokol | 23/259 X |
| 3,834,590 | 9/1974 | Robinson et al. | 73/425.6 X |

Primary Examiner—Joseph Scovronek
Attorney, Agent, or Firm—O'Brien & Marks

[57] ABSTRACT

An apparatus intended for a stepwise extraction of fluids, specifically for a dilution of liquid specimens. The apparatus comprises telescopically arranged suction pistons.

6 Claims, 1 Drawing Figure

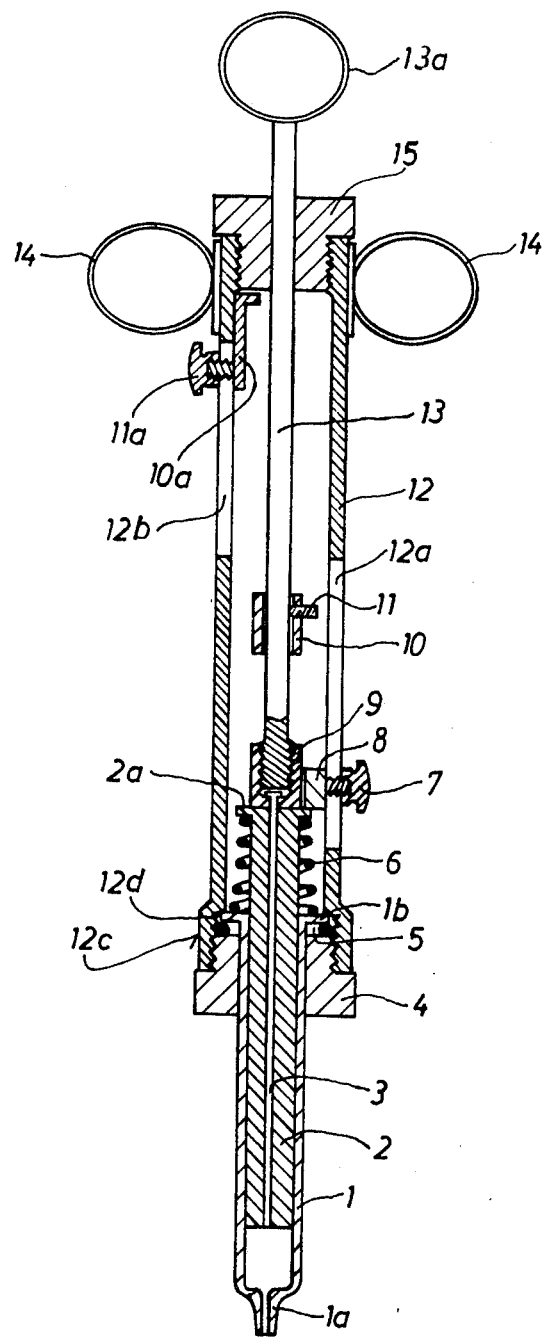

APPARATUS FOR DILUTION OF LIQUID SPECIMENS

BACKGROUND OF THE INVENTION

The present invention relates to a new and improved apparatus intended for a stepwise extraction of fluids specifically of a dilution of liquid specimens.

In numerous medical laboratories as well as in biological and chemical experimental of test laboratories oftentimes predetermined quantities of several reagents and other liquid components must be mixed or diluted. Quite often it is necessary to perform series of experiments featuring identical mixing or diluting procedures. With the present day apparatus one can not but settle with a time consuming and toilsome procedure according to which diversified liquids must be fed into a receptacle or mixing container by employing separate suction pipettes or other extraction implements.

SUMMARY OF THE INVENTION

Hence, it is a primary object of the present invention to provide on apparatus intended for a stepwise extraction of fluids specifically for a dilution of liquid specimens which apparatus comprises telescopically arranged suction pistons.

A further object of the invention is to provide an apparatus comprising two pistons both being coaxially moveable in the longitudinal direction of their stroke, comprising a spring retaining the outer of said two pistons in its upper dead center; comprising a chamber with a cover, a piston rod extending through said cover and being connected to the inner of said two pistons.

An other object of the ivnention is to provide an apparatus having a chamber comprising an abutment stop being releasably connected therewith and displaceable lengthwise thereof, an outer piston abutting in its dead center said abutment stop.

An other object of the invention is to provide an apparatus wherein the lower dead center of an inner piston is defined by the end portion of an outer piston positioned in a chamber and wherein the free end of the piston rod is provided with a gripping ring.

A further object of the invention is to provide an apparatus having a piston rod comprising a stop member releaseably connected therewith and displaceable thereon, said stop member abutting a cover of a chamber of the apparatus when an inner piston is located in its upper dead center.

Another object of the invention is to provide an apparatus comprising two pistons the strokes of which are fixed.

A further object of the invention is to provide an apparatus comprising exchangeable pistons.

BRIEF DESCRIPTION OF THE DRAWINGS

The invention will be better understood and objects other than those set forth above, will become apparent when consideration is given to the following detailed description thereof. Such description makes reference to the annexted drawings wherein the single FIGURE illustrates a longitudinal section of an embodiment of the inventive apparatus.

DETAILED DESCRIPTION OF THE PREFERRED EMBODIMENT

Describing now the drawing, a tubular chamber 12 made of a rigid plastics material is provided at its lower end with an integral collar 12c with thread, the internal diameter or bore of the chamber being suddenly increased thereat. A flange 1b of the cylindrical member 1 abuts a surface of the therewith formed shoulder 12d. The cylindrical member 12 consists of a translucent plastics material or glass, the cylindrical member being provided with a scale graduated in milliliters on its peripheral surface and with a conically tapered mouthpiece 1a which can be inserted into a hose. The flange 1b of the cylindrical member 12 is pressed against the surface of said shoulder 12d by means of a cap member 4 threadingly received in collar 12c with thread and provided with a passageway for the cylindrical member 12. For protection of flange 1b an elastic ring 5 is wedged between cap member 4 and flange 1b. An elongated piston 2 is slidingly received in the cylindrical member 1, the longitudinal extent thereof being larger than the longitudinal extent of the cylindrical member 1. The upper portion of the piston 2 projecting into the chamber 12 comprises an end flange 2a abutting a laterally mounted stop member 8. This stop member 8 is displaceable in the sidewall of the chamber 12 in an elongated slot 12c extending in the longitudinal direction of the chamber 12 and is held in any desired position by means of a knurled-head tightening screw 7. Accordingly, the stroke of the piston 2 can be freely chosen. The piston is provided with a central, axial through bore, in which a second piston 3 having substantially the same length as the piston 2 is slidingly received. Contrary to the outer piston 2 the inner piston 3 is provided with a piston rod 13, which is connected to the head portion of piston 3 by means of a cap screw 9, which extends through a cap 15 threadingly received in the chamber at the upper portion thereof, the cap providing at the one hand a guide for the piston rod 13 and at the other hand a stop surface for an abutting sleeve 10 fastened to the piston rod 13. The sleeve 10 is clamped on the piston rod 13 by means of a screw 11 with a hexagonal recessed hole. An elongated slot 12b extending parallel to the piston rod at the upper portion of the sidewall of the chamber allows the screw 11 to be loosened by means of a hexagon spanner passed through the slot 12b and thus the sleeve 10 to be shifted to a different position on the piston rod 13. Accordingly, the stroke of the inner piston 3 is also adjustable.

Obviously the sleeve can be fixedly anchored to the piston rod 13 and an L-shaped stop member 10a can be set onto the inner surface of the sidewall of the chamber together with a tightening screw 11a at the outer surface of the side wall of the chamber in slot 12b such as to vary the stroke of the inner piston 3.

The upper portion of the chamber is provided with two oppositely arranged gripping rings 14 and a gripping ring 13a is connected to the free end of the piston rod 13.

In use the index finger and the middle finger get inserted into gripping rings 14 and the thumb gets inserted into gripping ring 13a. By means of the thumb the piston rod 13 is urged farther into the chamber, pressing via cap screw 9 onto the outer piston 2 and pushing latter against the force of spring 6 and together with the inner piston 3 farther until the bottom dead center in the cylindrical member 1 is reached. The mouthpiece 1a or a hose connected to the mouth piece gets dipped into a first liquid. During release of the thumb both pistons 2,3 are brought together to the upper dead center of the outer piston 2 due to the flange 2a being urged by spring 6 against the stop member 8. Thus, a first quantity of liquid has been sucked up. The hose or the mouthpiece, resp., get replaced by a different one or dipped directly into a further, different liquid. Following, the gripping ring 13a together with the piston rod 13 get pulled upwardly by means of the thumb, until the sleeve 10 contacts the cap 15 or the L-shaped stop member 10a, resp., whereby the upper dead center of the inner piston 3 is arrived at. During the withdrawing of the piston rod a second quantity gets sucked up, whereby the slight turbelence caused by the withdrawal does not cause any substantial mixing of the liquid components. The ejection of the two components is achieved by a single push of the piston rod 13 into the chamber 13, whereby a thorough mixing is achieved.

The diameters of the inner piston as well as of the outer piston are to be chosen in accordance with prevailing conditions such that the piston displacement can also by changed by a change of said diameters.

Obviously a change of the diameter of the outer piston follows in employing a different cylindrical member and a different cap 4. A set consisting of two pistons 2,3 can by exchanged easily when utilizing an accordingly dimensioned cylindrical member 1 and accordingly fitted cap 4.

While there is shown and described the present preferred embodiment of the invention, it is to be distinctly understood that the invention is not limited thereto, but may be otherwise variously embodied and practiced within the scope of the following claims.

Accordingly, what is claimed is:

1. An apparatus for dilution of liquid specimens which comprises in combination, a tubular chamber having cap members disposed at opposite ends thereof, a cylindrical member projecting from one of said cap members, said cylindrical member having a restricted opening at one end for receiving fluids, a spring biased piston slidably disposed within the cylindrical member, means for limiting the movement of said spring biased piston out of the cylindrical member, a second piston axially disposed through a bore within the spring biased piston, said second piston having substantially the same length as the spring biased piston, a piston rod projecting through the opposite cap member and engaging the second piston by means of a head portion, said piston rod having externally disposed means for movement of the spring biased piston and the second piston respectively whereby controlled amounts of a liquid specimen may be introduced into the cylindrical member upon retraction of the spring biased piston, and further controlled amounts of a liquid specimen may be introduced into the cylindrical member upon retraction of the second piston.

2. The apparatus of claim 1 wherein the tubular chamber is provided with an abutment stop which is displaceable lengthwise along the tubular chamber, said spring biased piston having means for abutting said abutment stop at a dead end position.

3. The apparatus of claim 1 wherein the lower dead end position of said second piston is defined by the end portion of said spring biased piston, and the free end of said piston rod is provided with a gripping ring.

4. The apparatus of claim 1 wherein the piston rod is provided with a stop member which is displaceable thereon, said stop member abutting a cap member when the second piston is located at its upper withdrawn dead end position.

5. The apparatus of claim 1 wherein the stroke distance of the spring biased piston and of the second are fixed.

6. The apparatus of claim 1 having an elongated slot extending parallel to the piston rod at an upper portion of the sidewall of the tubular chamber, said slot having means to adjust the stroke distance of the second piston.

* * * * *